(12) United States Patent
Nagaraja et al.

(10) Patent No.: US 8,119,382 B2
(45) Date of Patent: Feb. 21, 2012

(54) VARIANT OF KPNI RESTRICTION ENDONUCLEASE

(75) Inventors: Valakunja Nagaraja, Bangalore (IN); Matheshwaran Saravanan, Bangalore (IN); Zhenyu Zhu, Beverly, MA (US)

(73) Assignees: New England Biolabs, Inc., Ipswich, MA (US); Indian Institute of Science, Bangalore (IN)

( * ) Notice: Subject to any disclaimer, the term of this patent is extended or adjusted under 35 U.S.C. 154(b) by 459 days.

(21) Appl. No.: 12/065,384

(22) PCT Filed: Aug. 18, 2006

(86) PCT No.: PCT/US2006/032519
§ 371 (c)(1),
(2), (4) Date: Feb. 29, 2008

(87) PCT Pub. No.: WO2007/027464
PCT Pub. Date: Mar. 8, 2007

(65) Prior Publication Data
US 2008/0227133 A1    Sep. 18, 2008

Related U.S. Application Data

(60) Provisional application No. 60/713,129, filed on Aug. 31, 2005.

(51) Int. Cl.
*C12N 9/22* (2006.01)
(52) U.S. Cl. ........................ 435/199; 435/193

(58) Field of Classification Search ............... None
See application file for complete search history.

(56) References Cited

U.S. PATENT DOCUMENTS 5,082,784 A    1/1992    Chatterjee et al.
5,192,675 A    3/1993    Chatterjee et al.

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Tomassini et al. Nucleic Acids Res. 5:4055-4064 (1978).
Kiss et al. Nucleic Acids Res. 19:3460 (1991).
Chandrashekaran et al. Nucleic Acids Res. 32:3148-3155 (2004).
Kosinski et al. Proteins 53:369-379 (2003).
Chandrashekaren et al., J. Biol. Chem. 279:49736-49740 (2004).
Xu et al., J. Bacteriology 173:5030 (1991).
Saravanan et al, Nucleic Acid Research 32:6129-6135 (2004).
Saravanan et al. Published Abstract: 5th New England Biolabs Meeting on Restriction/Modification Sep. 4-8, 2004.

* cited by examiner

*Primary Examiner* — Richard Hutson
(74) *Attorney, Agent, or Firm* — New England Biolabs, Inc; Harriet M. Strimpel

(57) ABSTRACT

Methods are provided for making restriction endonucleases with reduced star activity by one or more targeted mutations to a catalytic site within the restriction endonuclease. Examples of modifications to restriction endonucleases with significant sequence identity with KpnI are provided and reduced star activity demonstrated.

2 Claims, 4 Drawing Sheets

Figure 4

```
Query: 13   KNSYDQKTVSQRIEALFLNNLGKVVTRQQIIRAATDPKTGKQPENWHQRLSELRTDKGYT 71
            + Y Q++V +R+E  FL+NLGK+ TR+Q+I  A DP+TGK PENWHQR+SELRTD GYT
Sbjct: 51   SRKYTQESVVERLEVFFLDNLGKIATRKQLIEVAKDPNTGKIPENWHQRVSELRTDKGYT 110

Query: 72   ILSRRIMKVLAPQEYIMPHATRRPKAAKRVLPTKETRKQVLDRANYSCEWQELKQHCNLV 131
            I S +D+   L    KY+NP+A  +RP    +RV P+   TW  VL++    ++C N + G+ C+L
Sbjct: 111  IFSQKDLVFLRTSEYDKSPNAVKRPGTGRRVKPSATTWRRVLEKHKNTCAWDKGSEKCNLQ 170

Query: 132  KGDIDPIGGGTVKLTRDRMTPHSIDPATDVNDPKMNQALCSRHQVMKKNYRDSRMGKINV 191
            + DIDP+GGG V+LTPDH  RHS+DPA D NDP   NQ LCSRHQVM+K+N+ND   GK+NV
Sbjct: 171  KDDIDPVGGGRVRLTPDHKKPHSLDPAADANDPGANQPLCSRHQVMKFNPKDDKTGKLNV 230

Query: 192  IGILQSVNEKQNNDALEFLLNYYG 215   (SEQ ID NO:13)
            +GI+Q+ + K+K +A E L  ++G       (SEQ ID NO:15)
Sbjct: 231  LGIIQAASRKEKKEAYELLKEFYG 254   (SEQ ID NO:14)
```

VARIANT OF KPNI RESTRICTION ENDONUCLEASE

CROSS REFERENCE

This application is a §371 application of international application number PCT/US2006/032519 filed on Aug. 18, 2006, which claims priority from U.S. provisional application No. 60/713,129 filed Aug. 31, 2005, herein incorporated by reference.

BACKGROUND OF THE INVENTION

The KpnI restriction endonuclease is an orthodox Type IIP enzyme, which binds to DNA in the absence of metal ions and cleaves in the presence of $Mg^{2+}$. KpnI restriction endonuclease from *Klebsiella pneumoniae*, was characterized by Tomassini et al. *Nucleic Acids Res.* 5:4055-4064 (1978); Kiss et al. *Nucleic Acids Res.* 19:3460 (1991); Chandrashekaran et al. *Nucleic Acids Res.* 32:3148-3155 (2004) and cloned and sequenced as described in U.S. Pat. Nos. 5,192,675 and 5,082,784. KpnI is sold commercially in a buffer containing 10 mM Bis Tris Propane-HCl, 10 mM $MgCl_2$, 1 mM dithiothreitol (pH 7.0 at 25° C.) (New England Biolabs, Inc., Ipswich, Mass.).

KpnI recognizes the palindromic double-stranded hexameric DNA sequence 5'-GGTAC↓C-3' cleaving the DNA at the indicated position [↓] to generate a 3', 4-base overhang (Kosinski et al. *Proteins* 53:369-379 (2003)). KpnI restriction endonuclease forms a restriction-modification system together with KpnI methyltransferase, which transfers a methyl group from the cofactor AdoMet onto the $N^6$-position of the adenine in both strands within the same sequence.

SUMMARY

In an embodiment of the invention, a KpnI restriction endonuclease is provided in an effective cleavage buffer, the KpnI having reduced star activity for substrate DNA, compared with star activity of KpnI for the same substrate in 10 mM Bis Tris Propane-HCl, 10 mM $MgCl_2$, 1 mM dithiothreitol pH 7.0 at 25° C., as determined by gel electrophoresis.

In further embodiments of the invention, the effective cleavage buffer contains calcium ions.

Further embodiments of the invention provide a DNA encoding a modified KpnI restriction endonuclease; a host cell expressing the modified KpnI restriction endonuclease; and a modified KpnI restriction endonuclease. The modified KpnI restriction endonuclease is characterized by properties that include the following: having a catalytic motif PDX . . . D/EXK (SEQ ID NO:16) wherein one, or more amino acids in the motif are mutated; and having reduced star activity in a buffer for substrate DNA, compared with star activity of unmodified KpnI in the same buffer as determined by gel electrophoresis. In examples of mutations that result in reduced star activity, the one or more amino acid mutations may be a single mutation, for example D163 or K165, more particularly D163I or K165A; or two amino acid mutations, for example D163 and K165, more particularly D163I and K165A.

In a further embodiment of the invention, a method is provided for reducing star activity of a restriction endonuclease, that includes: (a) creating one or more mutations targeted to DNA encoding a catalytic site within DNA encoding the restriction endonuclease; (b) transforming a host cell with DNA encoding the mutated restriction endonuclease; (c) assaying the mutated restriction endonuclease produced by the transformed host cells for reduced star activity; and (d) selecting the restriction endonuclease with reduced star activity.

According to the method, the restriction endonuclease may be further defined as having at least 50%, 60%, 70%, 80% or 90% sequence homology with KpnI. Additionally, the one or more mutations may be targeted to amino acids in the PDX . . . D/EXK (SEQ ID NO:16) motif to generate a modified restriction endonuclease with reduced star activity. In a further embodiment, two mutations may be targeted to the PDX . . . D/EXK (SEQ ID NO:16) motif.

BRIEF DESCRIPTION OF THE DRAWINGS

Different amounts of KpnI restriction endonuclease were incubated with pUC18 DNA in assay buffer containing 5 mM $Mg^{2+}$ or $Mn^{2+}$ or $Ca^{2+}$ and 10 mM Tris-HCl (pH 7.4) at 37° C. for 1 h. The cleavage products were analyzed by 1% agarose gel electrophoresis. FIGS. 1D and 1E show cleavage of methylated plasmid DNA substrates by KpnI restriction endonuclease. The plasmids pUC18 (FIG. 1D) and pUCΔK (FIG. 1E) isolated from *E. coli* DH10B (pACMK) expressing KpnI methyltransferase were incubated with different concentrations of KpnI restriction endonuclease (0-100 units) in the presence of 5 mM $Mg^{2+}$.

The reactions were terminated by adding a mixture of 0.6% SDS and 25 mM EDTA. The samples were analyzed on 1% agarose gel. In each panel, Lane 0 represents the buffer control with the respective metal ions as indicated.

Figure 2:
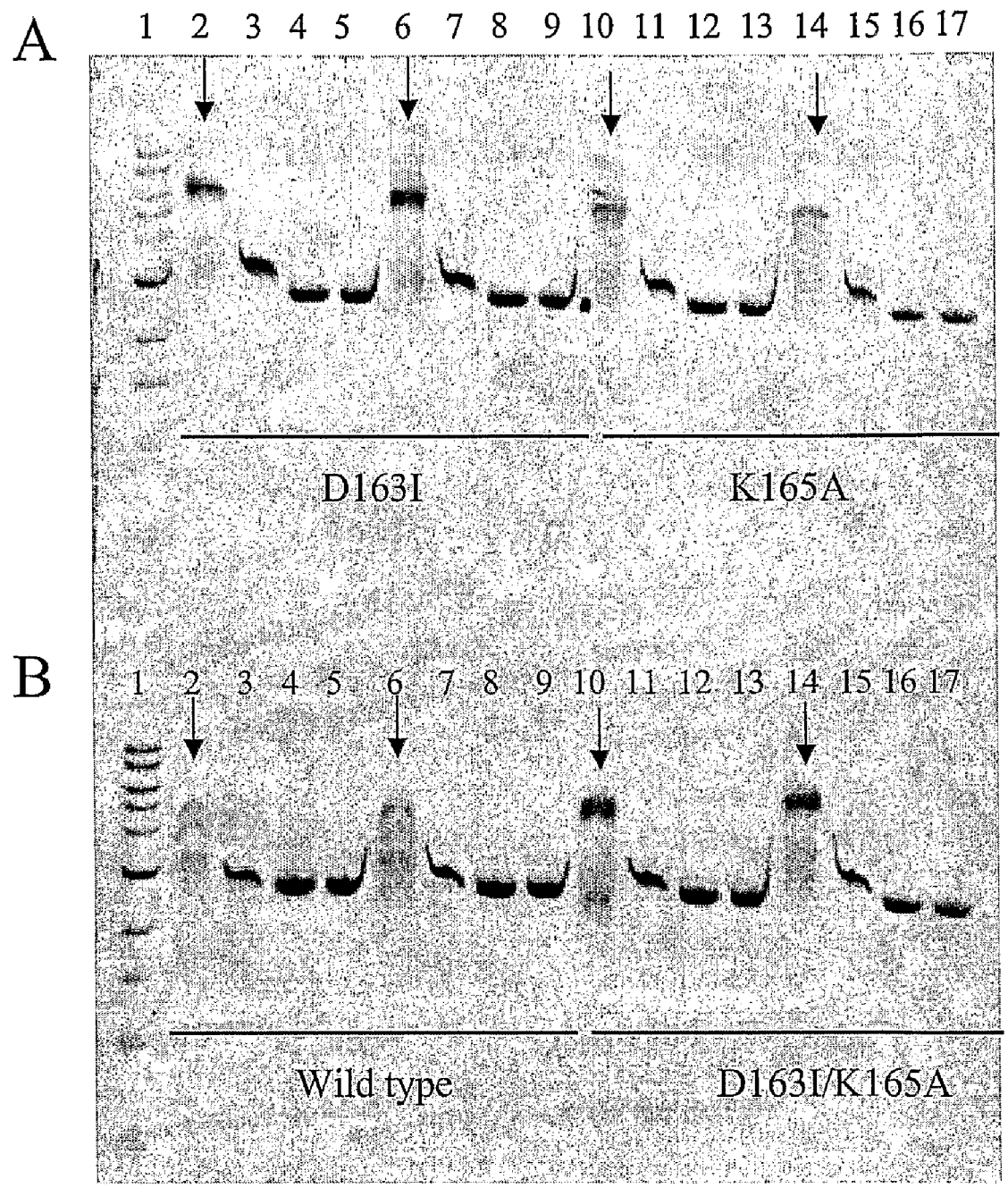

FIGS. 2A-2B show a comparison of cleavage activity using KpnI wild type and D163I/K165A, D163I and K165A mutants. The reaction conditions were: 3 µl of KpnI cell extract (approximately 4000 units of enzyme) were reacted with 0.5 µg pUC19 (one-site substrate with size 2.6 Kb) for 30 min at 37° C. in 1×NEB1 buffer (New England Biolabs, Inc., Ipswich, Mass.); the total reaction volume was 30 µl.

FIG. 2A: KpnI D163I and K165A:

Lane 1: NEB 1 kb DNA marker (New England Biolabs, Inc., Ipswich, Mass.);

Lanes 2-5: The D163I extract diluted at 1, 10, 100, 1000 fold (Lane 5). Lanes 6-9 duplicate Lanes 2-5;

Lanes 10-12: The K165A extract diluted at 1, 10, 100, 1000 fold (Lane 5); and

Lanes 13-16: duplicate of Lanes 10-12.

FIG. 2B: KpnI wild-type and D163I/K165A.

Lane 1: NEB 1 kb DNA marker (New England Biolabs, Inc., Ipswich, Mass.);

Lanes 2-5: The wild-type extract diluted at 1, 10, 100, 1000 fold;

Lanes 6-9: duplicate of Lanes 2-5.

Lanes 10-12: The D163I/K165A extract diluted at 1, 10, 100, 1000 fold;

Lanes 13-16: duplicate of Lanes 10-12.

The arrows indicate lanes containing undiluted endonuclease. At high concentrations, the wild-type has star activity, which is evident from the smears in Lanes 2 and 6 in FIG. 2B compared with the sharp bands in Lanes 2, 6, 10 and 14 in FIG. 2A and Lanes 10 and 14 in FIG. 2B. D163I has reduced star activity compared with K165A. The double mutant has still further reduced star activity.

Figure 3:
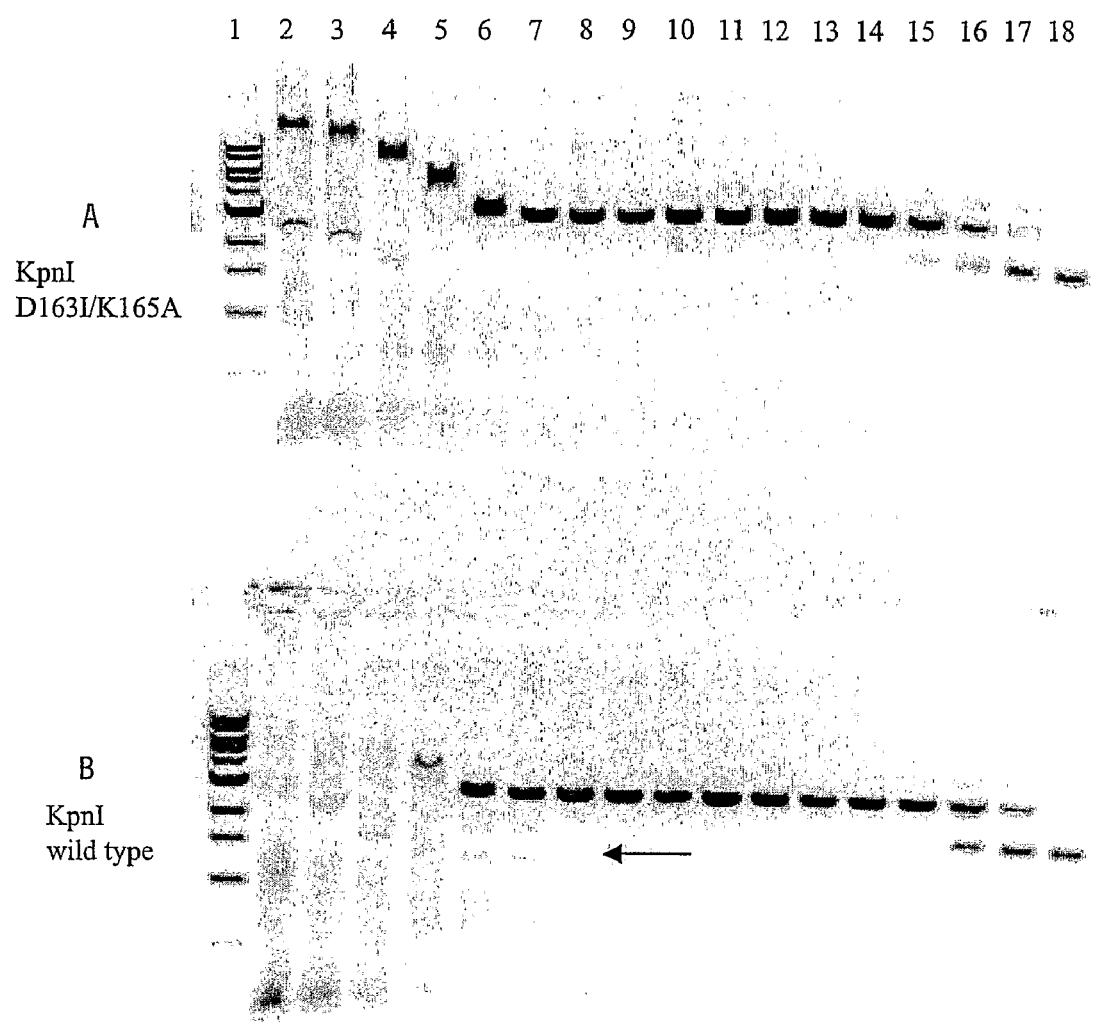

FIG. 3 show a comparison of KpnI wild-type (FIG. 3B) and D163I/K165A mutant KpnI (FIG. 3A) over an extended dilution range where the mutant shows significantly reduced star activity evan at 64 fold greater concentration compared with wild-type KpnI.

Lane 1:1 kb DNA marker (New England Biolabs, Inc., Ipswich, Mass.);

Lanes 2-17: The KpnI D163I/K165A (FIG. 3A) and wild type (FIG. 3B) each diluted at 1, 2, 4, 8, 16, 32, 64, 128, 256, 512, 1024, 2048, 4096, 8192, 16384, 32768 fold; 3 µl serial diluted extract digested 0.5 µg pUC19 in NEB1 at 37° C. for 1 hour (New England Biolabs, Inc., Ipswich, Mass.).

Lane 18: undigested pUC19.

The arrow in FIG. 3B points to the extra bands corresponding to cleavage fragments resulting from star activity of wild-type KpnI.

FIG. 4 shows sequence matching between the amino acid sequence for KpnI (SEQ ID NO:13) and the amino acid for CsyAM12ORFAP (SEQ ID NO:14).

The sequence comparison was achieved using the following parameters:
Query=KpnI
   (218 letters)
>CsyAM12ORFAP GGTACC
   Length=259
Score=263 bits (672), Expect=2e-75
Identities=112/204 (54%), Positives=150/204 (73%)
Matrix: BLOSUM62.

DETAILED DESCRIPTION OF THE EMBODIMENTS

It is well established that KpnI has star activity in $Mg^{2+}$ buffer. Star activity results from the recognition and cleavage of secondary cleavage sites in addition to a primary cleavage site. The secondary cleavage sites differ by one or more nucleotides from the primary recognition site. For KpnI, the primary cleavage site is GGTAC↓C. Secondary cleavage sites include tGTACC, GtTACC, GaTACC, GGaACC, GGTcCC, GGTAtC, GGTACg, and GGTACt.

Star activity for KpnI is generally observed in longer pieces of DNA substrates (greater then 1 kb) in which secondary cleavage sites are more likely to arise. Certain buffers such as 1.5 manganese buffers are more likely to favor star activity. In addition star activity is observed when the restriction endonuclease is present at increased concentrations (for example greater than 15 units). However, the cause or mechanism of star activity is not well understood either for KpnI or for other restriction endonucleases.

While not wishing to be limited by theory, KpnI is believed to have two catalytic sites so that inhibition of one of the sites (by, for example, calcium ions) or mutation (to inhibit cleavage activity) will reduce star activity. Any restriction endonuclease having significant sequence homology to KpnI such as CsyAM12OREAP (See FIG. 4) is believed to have star activity, which can be reduced in the presence of $Ca^{2+}$ or mutation(s) in one of its catalytic domains.

A structural and bioinformatic approach to analyzing promiscuous cleavage activity was undertaken by Chandrashekaren et al. (*J. Biol. Chem.* 279:49736-49740 (2004)) hereby incorporated by reference.

Although the properties of each restriction endonuclease is very variable from one endonuclease to another and there are no general rules about structure or sequence, some endonucleases have been noted to contain somewhere in their sequence, one or more $PDX_{10-30}(D/E)XK$ (SEQ ID NO:16) motifs involved in metal binding and DNA cleavage.

Bioinformatics analysis revealed that KpnI restriction endonuclease contains a ββαMe-finger fold, which is characteristic of many HNH-superfamily endonucleases. Members of the HNH-superfamily include homing endonuclease I-HmuI, structure-specific T4 endonuclease VII, colicin E9, sequence non-specific *Serratia* nuclease and sequence-specific homing endonuclease I-PpoI. In addition to the HNH catalytic site, KpnI also contains the PDX . . . D/EXK (SEQ ID NO:16) catalytic motif mentioned above. CsyAM12OREAP, which shares 54% sequence identity with KpnI, is expected to have a similar catalytic sequence and folding properties to KpnI. It is generally predicted that any restriction endonuclease sequence in GenBank having a sequence identity of about 30%, more particularly 40% more particularly 50% or greater will have a similar catalytic sequence and folding properties (see for example, CsyAM12OREAP, which has 54% amino acid sequence identity).

Once the catalytic sites of the KpnI were identified, individual amino acid residues were mutated within the sites. In specific embodiments, mutations at D148, H149 and Q175 of KpnI corresponding to the critical D, H and N or H residues of the HNH nucleases do not result in a change in star activity but instead resulted in loss of catalytic cleavage. For example, H149L mutant showed reduced DNA binding and complete loss of DNA cleavage in the presence of both $Mg^{2+}$ and $Mn^{2+}$. $Mg^{2+}$-mediated DNA cleavage was drastically reduced in selected mutants such as D148G and Q175E, while $Mn^{2+}$-mediated cleavage was not affected. The mutant Q175E fails to bind DNA at standard conditions, although the DNA binding and cleavage could be rescued at pH 6.0, indicating a role for Q175 in DNA binding and cleavage. While not wishing to be limited by theory, it is suggested that D148 and Q175 are involved in $Mg^{2+}$ coordination and H149 could be acting as a general base essential for DNA cleavage.

Mutation of amino acids in PDX . . . D/EXK (SEQ ID NO:16) surprisingly did not lead to loss of catalytic activity as observed for other restriction endonucleases (see for example, BamHI, Xu et al. *J. Bacteriology* 173:5030 (1991)). Instead when D163 or K165, which are part of the PDX14 D163 P164 K165 motif, were mutated, reduction in star activity was observed (see FIGS. 2A-2B and 3A-3B). A further reduction of star activity was observed when both D163 and K165 were mutated. The reduction of star activity was observed in standard magnesium buffer.

An unexpected reduction in star activity can also be achieved for wild-type KpnI when magnesium or manganese buffers are substituted with a calcium buffer (see FIGS. 1A-1E).

The present invention is further illustrated by the following Examples. These Examples are provided to aid in the understanding of the invention and should not be considered as a limitation thereof.

All references cited above and below are herein incorporated by reference including Chandrashekaren et al. *J. Biological Chemistry* 279:49736-49740 (2004), Saravanan et al. *Nucleic Acid Research* 32:6129-6135 (2004), Saravanan et al. Published Abstract: 5th New England Biolabs Meeting on Restriction/Modification Sep. 4-8, 2004 and U.S. Provisional Application No. 60/713,129 filed Aug. 31, 2005.

EXAMPLES

Example I

Sequence Alignment and Homology Modelling of KpnI

Protein Sequence Analysis and Structure Prediction

Sequence searches of the non-redundant database were carried out with PSI-BLAST (Kurowski And Bujnicki *Nucleic Acids Res.* 31:3305-3307 (2003)) via the NCBI website, (http://www.ncbi.nlm.nih.gov), using the sequence of T4 Endonuclease VII (EndoVII) as a query. An expectation (e)- value <10⁻³ was used to identify HNH-superfamily members related to EndoVII and build a multiple sequence alignment, subsequently converted to a position-specific scoring matrix (PSSM). The searches were iterated with the PSSM as a query until no more homologs with e-value <10⁻³ could be identified. Then, the cutoff was lowered to 0.1 and searches were continued with an additional criterion that potential HNH-superfamily members had to exhibit the residues of the common active site (otherwise, the sequences were not included in the PSSM). Protein structure prediction was carried out via the GeneSilico metaserver gateway [http://genesilico.pl/meta/ (Kosinski et al. *Proteins* 53:369-379 (2003). The sequence alignment between KpnI (Genbank X61796) and structurally characterized HNH-superfamily nucleases obtained from PSI-BLAST (after 15 iterations) was used as a starting point for homology modelling using the 'Frankenstein's monster' approach, comprising cycles of model building, evaluation, realignment in poorly scored regions and merging of best-scoring fragments (see Altschul et al. *Nucleic Acids Res.* 25:3389-3402 (1997)) for a detailed description. The positions of predicted catalytic residues and secondary structure elements were used as spatial restraints.

PSI-BLAST sequence searches of the non-redundant database revealed remote homology between EndoVII and KpnI (see also Aravind et al. *Nucleic Acids Res.* 28:3417-3432 (2000)). Our analyses resulted in a sequence alignment slightly different from that published in the earlier work (Aravind et al. *Nucleic Acids Res.* 28:3417-3432 (2000)). We confirmed the earlier prediction of the catalytic core, but also identified a potential Zn-finger conserved between KpnI and EndoVII, which were partially misaligned previously (Aravind et al. *Nucleic Acids Res.* 28:3417-3432 (2000)). In order to facilitate the interpretation of experimental data in the sequence-structure-function context, we built a theoretical model of the KpnI catalytic domain (residues 97-190) in complex with the target DNA. The homology model of the KpnI monomer was generated based on the sequence alignment with known structures of HNH-superfamily members. The mutual orientation of the two KpnI monomers as well as the coordinates of the DNA molecule and the Mg²⁺ ions were based on superposition onto the subunits A and B in the I-PpoI co-crystal structure (Galburt et al. *Nature Struct Biol.* 6:1096-1099 (1999)). The GGTACC site recognized by KpnI was generated by 'mutating' bases in the original I-PpoI target (CTTAAG) and optimizing their geometry using HyperChem 7.1 (Hypercube, Inc., Gainesville, Fla.). The final model of the KpnI dimer complexed with the GGTACC sequence (available for download from ftp://genesilico.pl/iamb/models/KpnI/) was obtained after steric clashes between a few residues from both monomers and the DNA was removed by selecting different rotamers of the respective side chains.

Example II

Generation of Site-Directed Mutants for D148, H149 And Q175

Enzymes and DNA

Plasmid pETRK contains the wild-type KpnI restriction endonuclease gene cloned into the pET11d expression vector (Chandrashekaran et al. *J. Biosci* 24:269-277 (1999)). KpnI restriction endonuclease and its mutants were purified as described previously (Chandrashekaran et al. *J. Biosci* 24:269-277 (1999)). The enzymes were diluted in binding buffer [20 mM Tris-HCl (pH 7.4), 25 mM NaCl and 5 mM 2-mercaptoethanol] for all the studies. The concentration of the proteins was estimated by the method of Bradford (*Anal. Biochem.* 72:248-254 (1976)). T4 polynucleotide kinase, Pfu DNA polymerase and DpnI were purchased from New England Biolabs, Inc. (Ipswich, Mass.) for use in inverse PCR. Oligonucleotide primers (Microsynth Inc, Balgach, Switzerland) were purified on 18% urea-polyacrylamide gel (Sambrook et al. *Molecular Cloning: A Laboratory Manual*, Cold Spring Harbor Laboratory Press, Cold Spring Harbor, N.Y., pp. 35-38 (1989)). The purified oligonucleotides were end-labeled with T4 polynucleotide kinase and [λ-³²P]ATP (6000 Ci/mmol).

Site-Directed Mutagenesis

KpnI restriction endonuclease mutants were generated by site-directed mutagenesis using the megaprimer inverse PCR method (Kirsch and Joly, *Nucleic Acids Res.* 26:1848-1850 (1998))). Expression plasmid pETRK encoding the wild-type kpnR gene was used as a template. The oligonucleotide primers carrying the respective mutant amino acid codon substitutions were used as forward primers. These were as follows:

```
D148G:
5'CTAACACCTGGCCATATGACAC-3'         (SEQ ID NO:1)

H149L:
5' ACACCAGACCTTATGACACCTC-3'        (SEQ ID NO:2)

Q175E:
5'-TGTGGACGTTCATGAAGTTATGAAA -3'    (SEQ ID NO:3)

D148A:
5'- AACTAACACCAGCCCATATGACA-3'      (SEQ ID NO:4)

H149A:
5'- ACACCAGACGCTATGACACCTC-3'       (SEQ ID NO:5)
and

T7 terminator primer was used as reverse
primer:
5'-GCTAGTTATTGTTCAGCGGTGGG -3'      (SEQ ID NO:6)
```

The mega primers generated were used as complementary primers for the second round of PCR amplification. After confirming the mutation by sequencing, the mutant restriction endonucleases were expressed in *E. coli* BL26 [F⁻ ompT hsdS$_B$ (r$_B$-m$_B$-) gal dcm Δlac (DE3) nin5 lac UV5-T7 gene 1] expressing M.KpnI and purified as described previously (Chandrashekaran et al. *J. Biosci.* 24:269-277 (1999)).

The homology model of KpnI restriction endonuclease reveals the ββα-Me finger fold composed of two antiparallel β-strands, an α-helix and a metal ion, between the first strand and the helix. Based on the bioinformatics analysis, amino acid residues D148, H149 and Q175 of KpnI restriction endonuclease are predicted to be functionally equivalent to the catalytic/metal-binding residues D40, H41 and N62 of T4 EndoV11 (Raaijmakers et al. *J. Mol. Biol.* 308:311-323 (2001)), and the corresponding residues of other HNH nucleases. Thus, D148, H149 and Q175 were targeted for mutagenesis. The mutations were confirmed by restriction digestion and sequencing analysis. The mutant kpnIR genes present in the pET11d vector were expressed in *E. coli* BL26 and the mutant proteins were purified. During purification steps, all the mutants exhibited properties similar to that of wild-type enzyme, suggesting that they were properly folded.

Example III

Cleavage and Binding Activity of KpnI Mutants (D148, H149 And 0175)

Electrophoretic Mobility Shift Assay

Different concentrations of the wild-type and mutant KpnI restriction endonuclease (0.1-128 nM) were incubated with 3.75 nM of end-labeled double-stranded oligonucleotides containing cognate site in the buffers [20 mM Tris-HCl (pH 7.4), 25 mM NaCl and 5 mM 2-mercaptoethanol or 20 mM HEPES (pH 6.0), 25 mM NaCl and 5 mM 2-mercaptoethanol] on ice for 15 min. The free DNA and the enzyme-bound complexes were then separated on 8% native polyacrylamide gels with running buffers containing 90 mM Tris-borate pH 8.0 and 1 mM EDTA or 50 mM HEPES, pH 6.0 and 1 mM EDTA. The gels were electrophoresed at 4° C. for 1 h, dried and autoradiographed. The amounts of DNA in free and bound form were quantitated using Phosphorimager Image Gauge software version 2.54. The assays were repeated three times and the average values were considered for Scatchard analysis to determine the affinity of the proteins.

In Vitro DNA Cleavage Activity Assay

Purified KpnI restriction endonuclease and its mutants were incubated in 20 mM HEPES-KOH (pH 6.0) or 10 mM Tris-HCl (pH 7.0-9.0), 1 mM EDTA, 5 mM β-mercaptoethanol, 5 mM $MgCl_2$ for 1 h at 37° C. and 500 ng of plasmid DNA. The cleavage products were analyzed on 1% agarose gel.

Wild-type KpnI restriction endonuclease and its mutants were assayed for the ability to cleave DNA. pUC18 DNA was completely linearized by 1 nM wild-type enzyme. Under the same assay conditions, no cleavage product was detected with the mutant H149L even at 100-fold excess protein concentrations. Mutant H149A also behaved in the same fashion. Mutants D148G and Q175E showed only traces of the DNA cleavage activity when used in large excess. Similar results were observed with D148A. In order to measure the residual activity more precisely, reactions were performed with higher concentrations of D148G and Q175E. No complete linearization of the DNA substrate could be observed even at 2 μM (2000-fold excess) of the enzyme concentration. However, prolonged incubation for 12 h resulted in near-complete DNA cleavage with D148G, while the pattern with H149L and Q175E did not change significantly under standard assay conditions. In contrast, incubation with very low amounts of the wild-type enzyme (0.05 units) for prolonged incubation lead to complete DNA cleavage. Thus, all three residues of the predicted HNH motif were found to be essential for the restriction endonuclease activity.

Example IV

Metal Ion-Dependent Cleavage Reactions

Enzymes and DNA

KpnI restriction endonuclease was purified as described previously (Tomassini et al. *Nucleic Acids Res.* 5:4055-4064 (1988)). The enzyme was diluted in binding buffer (20 mM Tris-HCl (pH 7.4), 25 mM NaCl, and 5 mM 2-mercaptoethanol) for all the studies. The concentration of the enzyme was estimated by the method of Bradford (*Anal. Biochem.* 72:248-254 (1976)). One unit of KpnI Restriction endonuclease is defined as the amount of enzyme required for complete digestion of 1 μg of λDNA at 37° C. for 1 h by using assay buffer containing 5 mM $Mg^{2+}$.

Restriction Endonuclease Digestion

Standard assay conditions involved lower enzyme units to DNA ratio (up to 10 units of enzyme), whereas in relaxed assay conditions, more than 15 units of enzyme were used. Digestions were carried out by incubating different units of KpnI restriction endonuclease with plasmid DNA or 0.2 pmol of labeled oligonucleotides in assay buffer containing 10 mM Tris-HCl (pH 7.4), 5 mM β-mercaptoethanol, and appropriate concentrations of divalent metal ions at 37° C. for 1 h. The reactions were terminated by adding stop dye containing 0.6% SDS and 25 mM EDTA. The cleavage products of plasmid DNA and oligonucleotides were analyzed on 1% agarose or 12% urea-polyacrylamide gel, respectively. The $Ca^{2+}$ chase reactions were carried out at a fixed concentration of $Mg^{2+}$ (2 mM) or $Mn^{2+}$ (0.5 mM) by using increasing concentrations of $Ca^{2+}$.

The effect of divalent metal ions (FIGS. 1A-1E) on the activity of KpnI restriction endonuclease was studied by using plasmid DNA as substrates (for example, pUC18 or pACMK (from New England Biolabs, Inc., Ipswich, Mass.). KpnI restriction endonuclease exhibits relaxed specificity at high enzyme to substrate ratios. A high degree of promiscuous activity was observed when more than 15 units of the enzyme were used in the presence of $Mg^{2+}$ (FIG. 1A).

KpnI restriction endonuclease exhibits specific DNA cleavage in presence of $Ca^{2+}$ (FIG. 1C) showing greater specificity at high enzyme to substrate ratios in contrast to the cleavage pattern with $Mg^{2+}$.

Figure 1:
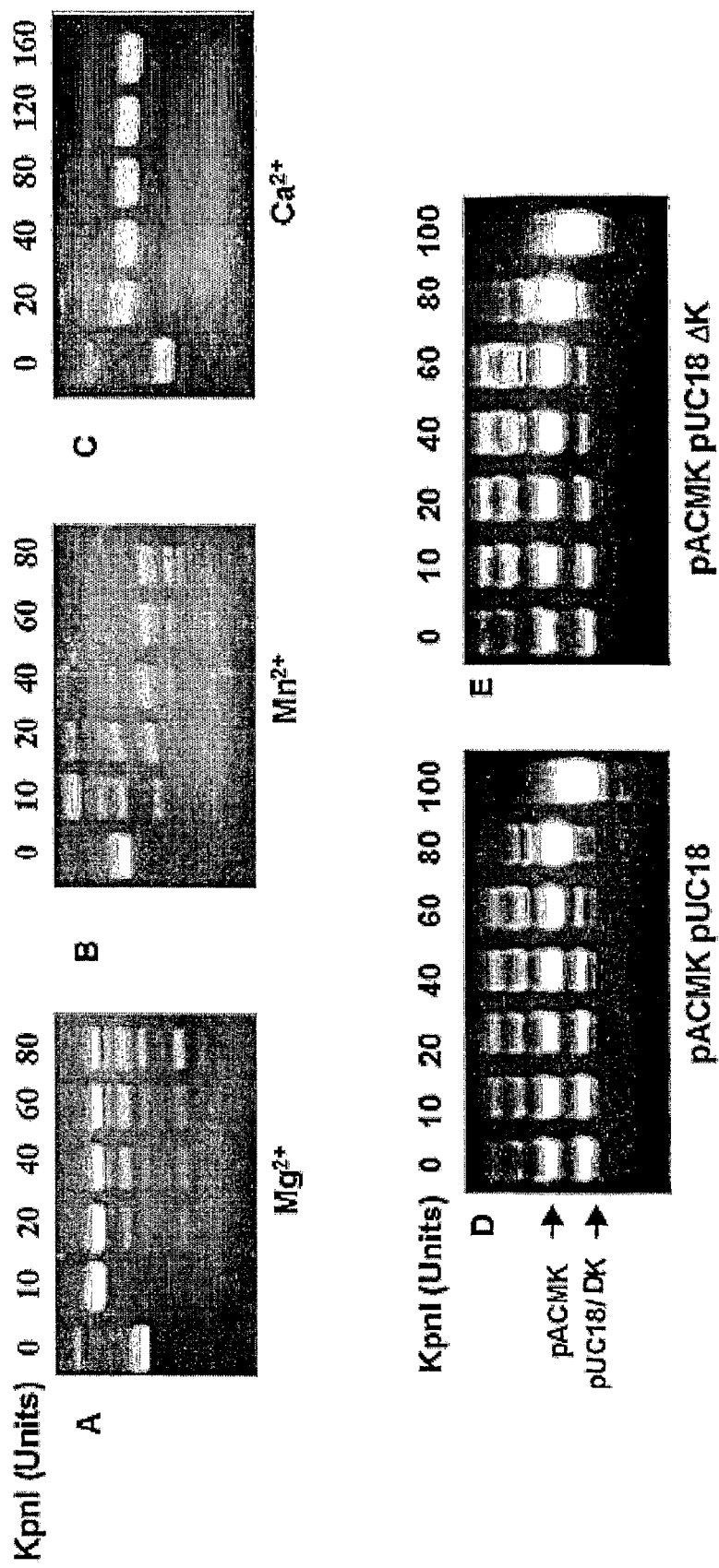
FIGS. 1A-1E show promiscuous cleavage by wild-type KpnI restriction endonuclease. Plasmid DNA was cleaved by KpnI in the presence $Mg^{2+}$ (FIG. 1A), $Mn^{2+}$ (FIG. 1B), and $Ca^{2+}$ (FIG. 1C).

No DNA cleavage was detected at the noncanonical sites in the presence of $Ca^{2+}$ even at a high enzyme to substrate ratio (FIG. 1C). The $Ca^{2+}$-mediated DNA cleavage is confined to the canonical site irrespective of plasmid or oligonucleotide substrates.

Example V

Overexpression of Mutant Kpn1 (D163I and K165A)

Construction of Pre-Modified Strain

The plasmid pSYX20-KpnIM and pAGR3-KpnIR was extracted from NEB strain 977 by standard Qiagen miniprep kit (Qiagen, Valencia, Calif.). The mixture of plasmids was used to transform ER2502 by chemical means. The transformants were plated on Kanamycin (Kan) plates. Ten of the transformed colonies were picked and each transformant was checked to determine the presence of a single plasmid. The genomic DNA from these cells was also checked for protective modification against KpnI digestion. These colonies were grown and made into chemical competent cells.

Construction of the KpnI mutants: D163I, K165A and D163I/K165A

KpnI mutants D163I, K165A and D163/K165A were constructed by inverse PCR. The PCR primers were as following:

(SEQ ID NO:7)
5' CCCGCAACTGATGTAAATATTCCTAAAATGTGGCAAGCA 3'
(D163IF)

(SEQ ID NO:8)
5' TGCTTGCCACATTTTAGGAATATTTACATCAGTTGCGGG 3'
(D163IR)

(SEQ ID NO:9)
5' ACTGATGTAAATGATCCTGCAATGTGGCAAGCATTGTGT 3'
(K165AF)

(SEQ ID NO:10)
5' ACACAATGCTTGCCACATTGCAGGATCATTTACATCAGT 3'
(K165AR)

(SEQ ID NO:11)
5' CCCGCAACTGATGTAAATATTCCTGCAATGTGGCAAGCATTGTGT 3' (D163I/K165AF)

(SEQ ID NO:12)
5' ACACAATGCTTGCCACATTGCAGGAATATTTACATCAGTTGCGGG 3' (D163I/K165AR)

The PCR composition was as follows: 1 μl pAGR3—KpnIR as template, 2 μl each of the primers, 4 μl 10 mM dNTP, 10 μl 10× Thermopol buffer, 2 μl Deep Vent DNA polymerase (4 units) (New England Biolabs, Inc., Ipswich, Mass.); 0, 2, or 6 μl 100 mM MgSO₄. H₂O was added to a final volume of 100 μl. The reaction condition was: 94° C. 5 min, followed by 20 cycles of 94° C. 30 sec, 55° C. 30 sec and 72° C. 6 min and 36 sec, and a final 72° C. for 7 min. 4 μl PCR product was treated with 40 units of DpnI and then transformed into ER2502-[pSYX20-KpnIM] and selected on ampiciillin- and kanamycin-containing plates. Four colonies corresponding to each of the transformants were grown and plasmid DNA extracted and sequenced to confirm the presence of the desired mutations.

Comparison of the KpnI wild-type and mutants D163I, K165A, and D163I/K165A

Two of the colonies were grown into 10 ml overnight cultures. 200 μl of each overnight culture were inoculated into 10 ml LB with ampicillin and kanamycin. After 5 hours growth, the cells were induced with 0.5 mM IPTG (isopropyl-beta-D-thiogalactopyranoside) and grown overnight. The cultures were spun down and sonicated in 1 ml sonication buffer (10 mM pH7.5 Tris-HCl, 50 mM NaCl, and 10 mM β-Me). The extracts were diluted 10, 100 or 1000 fold, and 3 μl from each dilution were reacted with 0.5 μg pUC19 (one-site substrate) for 30 min at 37° C. in 1×NEB1 buffer (New England Biolabs, Inc., Ipswich, Mass.). The digested pUC19 was run on 0.8% agarose gel. At undiluted concentration of the extract, the wild-type KpnI digested pUC19 into multiple bands (star activity), while the D163I/K165A, D163I and K165A mutant KpnI all showed enhanced amounts of single band cleavage product compared with wild-type KpnI. At a high protein concentration, the DNA band was bound and retarded in the gel. A comparison of the mutants revealed that the double KpnI mutant D163I/K165A yielded cleavage product with the least star activity compared with the single mutants. A side-by-side comparison was made again for KpnI D163I/K165A with wild-type at 1:2 serial dilution. 3 μl serial diluted extract digested 0.5 μg pUC19 in NEB1 at 37° C. for 1 hour (New England Biolabs, Inc., Ipswich, Mass.). The KpnI D163I/K165A retained the same specific activity to turn pUC19 from super-coiled form to linear form, while it cleaved pUC19 into a single band. In contrast, wild-type KpnI digested pUC19 into multiple bands. The KpnI D163I/K165A was found to have no more than 1/64 of the wild-type KpnI star activity, and could be expressed in a host cell preparation at 10,000,000 units/gram of wet cells.

What is claimed is:

1. A variant KpnI restriction endonuclease having at least 90% sequence identity with SEQ ID NO: 13 wherein
the amino acid at the position corresponding to amino acid 163 of SEQ ID NO: 13 is not Asp (D);
the amino acid at the position corresponding to amino acid 165 of SEQ ID NO: 13 is not Lys (K);
the amino acid at the position corresponding to amino acid 148 of SEQ ID NO: 13 is not a Asp (D);
the amino acid at the position corresponding to amino acid 175 of SEQ ID NO: 13 is not Gln (Q);
or
the amino acids at the positions corresponding to amino acids 163 and 165 of SEQ ID NO: 13 are not Asp (D) and Lys (K), respectively.

2. The variant KpnI restriction endonuclease according to claim 1 having an amino acid sequence consisting essentially of SEQ ID NO: 13, wherein
the amino acid at the position corresponding to amino acid 163 of SEQ ID NO: 13 is not Asp (D);
the amino acid at the position corresponding to amino acid 165 of SEQ ID NO: 13 is not Lys (K);
the amino acid at the position corresponding to amino acid 148 of SEQ ID NO: 13 is not a Asp (D);
the amino acid at the position corresponding to amino acid 175 of SEQ ID NO: 13 is not Gln (Q);
or
the amino acids at the positions corresponding to amino acids 163 and 165 of SEQ ID NO: 13 are not Asp (D) and Lys (K), respectively.

* * * * *

```
                        SEQUENCE LISTING

<160> NUMBER OF SEQ ID NOS: 16

<210> SEQ ID NO 1
<211> LENGTH: 22
<212> TYPE: DNA
<213> ORGANISM: unknown
<220> FEATURE:
<223> OTHER INFORMATION: primer

<400> SEQUENCE: 1
ctaacacctg gccatatgac ac                                            22

<210> SEQ ID NO 2
<211> LENGTH: 22
<212> TYPE: DNA
<213> ORGANISM: unknown
<220> FEATURE:
<223> OTHER INFORMATION: primer

<400> SEQUENCE: 2
acaccagacc ttatgacacc tc                                            22

<210> SEQ ID NO 3
<211> LENGTH: 25
<212> TYPE: DNA
<213> ORGANISM: unknown
<220> FEATURE:
<223> OTHER INFORMATION: primer

<400> SEQUENCE: 3
tgtggacgtt catgaagtta tgaaa                                         25

<210> SEQ ID NO 4
<211> LENGTH: 23
<212> TYPE: DNA
<213> ORGANISM: unknown
<220> FEATURE:
<223> OTHER INFORMATION: primer

<400> SEQUENCE: 4
aactaacacc agcccatatg aca                                           23
```

<210> SEQ ID NO 5
<211> LENGTH: 22
<212> TYPE: DNA
<213> ORGANISM: unknown
<220> FEATURE:
<223> OTHER INFORMATION: primer

<400> SEQUENCE: 5
acaccagacg ctatgacacc tc					22

<210> SEQ ID NO 6
<211> LENGTH: 23
<212> TYPE: DNA
<213> ORGANISM: unknown
<220> FEATURE:
<223> OTHER INFORMATION: primer

<400> SEQUENCE: 6
gctagttatt gttcagcggt ggg					23

<210> SEQ ID NO 7
<211> LENGTH: 39
<212> TYPE: DNA
<213> ORGANISM: unknown
<220> FEATURE:
<223> OTHER INFORMATION: primer

<400> SEQUENCE: 7
cccgcaactg atgtaaatat tcctaaaatg tggcaagca			39

<210> SEQ ID NO 8
<211> LENGTH: 39
<212> TYPE: DNA
<213> ORGANISM: unknown
<220> FEATURE:
<223> OTHER INFORMATION: primer

<400> SEQUENCE: 8
tgcttgccac attttaggaa tatttacatc agttgcggg			39

<210> SEQ ID NO 9
<211> LENGTH: 39
<212> TYPE: DNA
<213> ORGANISM: unknown
<220> FEATURE:
<223> OTHER INFORMATION: primer

<400> SEQUENCE: 9
actgatgtaa atgatcctgc aatgtggcaa gcattgtgt			39

<210> SEQ ID NO 10
<211> LENGTH: 39
<212> TYPE: DNA
<213> ORGANISM: unknown
<220> FEATURE:
<223> OTHER INFORMATION: primer

<400> SEQUENCE: 10
acacaatgct tgccacattg caggatcatt tacatcagt			39

<210> SEQ ID NO 11
<211> LENGTH: 45
<212> TYPE: DNA
<213> ORGANISM: unknown
<220> FEATURE:
<223> OTHER INFORMATION: primer

<400> SEQUENCE: 11
cccgcaactg atgtaaatat tcctgcaatg tggcaagcat tgtgt                45

<210> SEQ ID NO 12
<211> LENGTH: 45
<212> TYPE: DNA
<213> ORGANISM: unknown
<220> FEATURE:
<223> OTHER INFORMATION: primer

<400> SEQUENCE: 12
acacaatgct tgccacattg caggaatatt tacatcagtt gcggg                45

<210> SEQ ID NO 13
<211> LENGTH: 204
<212> TYPE: PRT
<213> ORGANISM: unknown
<220> FEATURE:
<223> OTHER INFORMATION: Klebsiella pneumoniae OK8

<400> SEQUENCE: 13

Asn Asn Ser Tyr Asp Gln Lys Thr Val Ser Gln Arg Ile Glu Ala Leu
1               5                   10                  15

Phe Leu Asn Asn Leu Gly Lys Val Val Thr Arg Gln Gln Ile Ile Arg
            20                  25                  30

Ala Ala Thr Asp Pro Lys Thr Gly Lys Gln Pro Glu Asn Trp His Gln
        35                  40                  45

Arg Leu Ser Glu Leu Arg Thr Asp Lys Gly Tyr Thr Ile Leu Ser Trp
    50                  55                  60

Arg Asp Met Lys Val Leu Ala Pro Gln Glu Tyr Ile Met Pro His Ala
65                  70                  75                  80

Thr Arg Arg Pro Lys Ala Ala Lys Arg Val Leu Pro Thr Lys Glu Thr
                85                  90                  95

Trp Glu Gln Val Leu Asp Arg Ala Asn Tyr Ser Cys Glu Trp Gln Glu
            100                 105                 110

Asp Gly Gln His Cys Gly Leu Val Glu Gly Asp Ile Asp Pro Ile Gly
        115                 120                 125

Gly Gly Thr Val Lys Leu Thr Pro Asp His Met Thr Pro His Ser Ile
    130                 135                 140

Asp Pro Ala Thr Asp Val Asn Asp Pro Lys Met Trp Gln Ala Leu Cys
145                 150                 155                 160

Gly Arg His Gln Val Met Lys Lys Asn Tyr Trp Asp Ser Asn Asn Gly
                165                 170                 175

Lys Ile Asn Val Ile Gly Ile Leu Gln Ser Val Asn Glu Lys Gln Lys
            180                 185                 190

Asn Asp Ala Leu Glu Phe Leu Leu Asn Tyr Tyr Gly
        195                 200

<210> SEQ ID NO 14
<211> LENGTH: 204
<212> TYPE: PRT
<213> ORGANISM: unknown
<220> FEATURE:
<223> OTHER INFORMATION: Cenarchaeum symbiosum C18HII

<400> SEQUENCE: 14

Ser Arg Lys Tyr Thr Gln Glu Ser Val Val Glu Arg Leu Glu Val Phe
1               5                   10                  15

Phe Leu Asp Asn Leu Gly Lys Ile Ala Thr Arg Lys Gln Leu Ile Glu

-continued

```
                 20                  25                  30
Val Ala Lys Asp Pro Arg Thr Gly Lys Ile Pro Glu Asn Trp His Gln
            35                  40                  45

Arg Val Ser Glu Leu Arg Thr Asp His Gly Tyr Thr Ile Phe Ser Gln
        50                  55                  60

Lys Asp Leu Val Phe Leu Lys Thr Ser Glu Tyr Met Met Pro Asn Ala
65                  70                  75                  80

Val Lys Arg Pro Gly Thr Gly Arg Arg Val Lys Pro Ser Ala Thr Thr
                85                  90                  95

Trp Arg Ser Val Leu Glu Lys His Lys His Thr Cys Ala Trp Asp Lys
            100                 105                 110

Gly Gly Glu Lys Cys Gly Leu Gln Lys Asp Asp Ile Asp Pro Val Gly
        115                 120                 125

Gly Gly Arg Val Arg Leu Thr Pro Asp His Lys Lys Pro His Ser Leu
    130                 135                 140

Asp Pro Ala Ala Asp Ala Asn Asp Pro Ser Ala Trp Gln Pro Leu Cys
145                 150                 155                 160

Gly Arg His Gln Val Met Lys Lys Asn Phe Trp Asp Asp Lys Thr Gly
                165                 170                 175

Lys Leu Asn Val Leu Gly Ile Ile Gln Ala Ala Ser Arg Lys Glu Lys
            180                 185                 190

Lys Glu Ala Tyr Glu Leu Leu Lys Glu Phe Phe Gly
        195                 200

<210> SEQ ID NO 15
<211> LENGTH: 112
<212> TYPE: PRT
<213> ORGANISM: artificial
<220> FEATURE:
<223> OTHER INFORMATION: consensus sequence

<400> SEQUENCE: 15

Tyr Gln Val Arg Glu Phe Leu Asn Leu Gly Lys Thr Arg Gln Ile Ala
1               5                   10                  15

Asp Pro Thr Gly Lys Pro Glu Asn Trp His Gln Arg Ser Glu Leu Arg
            20                  25                  30

Thr Asp Gly Tyr Thr Ile Ser Asp Leu Glu Tyr Met Pro Ala Arg Pro
        35                  40                  45

Arg Val Pro Thr Trp Val Leu Cys Trp Gly Cys Gly Leu Asp Ile Asp
    50                  55                  60

Pro Gly Gly Gly Val Leu Thr Pro Asp His Pro His Ser Asp Pro Ala
65                  70                  75                  80

Asp Asn Asp Pro Trp Gln Leu Cys Gly Arg His Gln Val Met Lys Lys
                85                  90                  95

Asn Trp Asp Gly Lys Asn Val Gly Ile Gln Lys Lys Ala Glu Leu Gly
            100                 105                 110

<210> SEQ ID NO 16
<211> LENGTH: 7
<212> TYPE: PRT
<213> ORGANISM: artificial
<220> FEATURE:
<223> OTHER INFORMATION: catalytic motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
```

-continued

```
<223> OTHER INFORMATION: Xaa can be any naturally occurring amino acid

<400> SEQUENCE: 16

Pro Asp Xaa Asp Glu Xaa Lys
1               5
```